US006399778B1

(12) United States Patent
LaBell et al.

(10) Patent No.: US 6,399,778 B1
(45) Date of Patent: Jun. 4, 2002

(54) SYNTHESIS OF 3-[4-(2-AMINOETHOXY)-BENZOYL]-2-ARYL-6-HYDROXYBENZO[B]THIOPHENES

(75) Inventors: Elizabeth Smith LaBell; John McNeill McGill; Randal Scot Miller, all of Lafayette, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 08/469,093

(22) Filed: Jun. 6, 1995

Related U.S. Application Data

(60) Division of application No. 08/427,914, filed on Apr. 26, 1995, now abandoned, which is a continuation-in-part of application No. 08/308,325, filed on Sep. 19, 1994, now Pat. No. 5,629,425.

(51) Int. Cl.[7] ............... C07D 409/06; C07D 333/04
(52) U.S. Cl. ............... 546/202; 549/57; 548/525; 544/146; 544/376; 540/596
(58) Field of Search ............... 540/596; 544/146, 544/376; 546/202; 548/525; 569/57

(56) References Cited

U.S. PATENT DOCUMENTS

| | | | | |
|---|---|---|---|---|
| 3,869,485 A | * | 3/1975 | DeLong | 562/857 |
| 4,133,814 A | | 1/1979 | Jones et al. | 548/525 |
| 4,358,593 A | | 11/1982 | Jones et al. | 546/202 |
| 4,380,635 A | | 4/1983 | Peters | 546/202 |
| 4,418,068 A | | 11/1983 | Jones | 514/337 |
| 5,169,860 A | | 12/1992 | Mohamadi et al. | 514/415 |
| 5,470,854 A | | 11/1995 | von Angerer et al. | 514/233.5 |
| 5,512,684 A | | 4/1996 | Alt | 549/51 |

FOREIGN PATENT DOCUMENTS

| | | | |
|---|---|---|---|
| CA | 2110062 AA | 12/1992 | C07D/307/79 |
| EP | 0062503 | 10/1982 | C07D/333/56 |
| EP | 0062504 | 10/1982 | C07D/333/56 |
| EP | 0062505 | 10/1982 | C07D/333/56 |
| EP | 0605193 | 7/1994 | A61K/31/40 |
| EP | 0635264 | 1/1995 | A61K/31/135 |
| GB | 2097788 | 11/1982 | C07D/409/12 |
| WO | WO 95/10513 | 4/1995 | C07D/333/56 |

OTHER PUBLICATIONS

Knight "Its time to stop discrimination against PCT/USA national phase patents" JPTOS Jun., p.386–400, 1997.*
Evans "Chrystal Chemistry" Cambridge Press, p.393–397, 1964.*
Okumura et al. "Preparation of N–acyllactam derivatives as alcohol fermentation enhancing agents" CA 110:8054f, 1989.*
Zhu et al. "Synthesis of bisflavone–type compounds (III). Selective demethoxylation of 1,4–bis(2',4',6'–trimethoxtphenyl)–1,4–butanedione" CA 112:197755k, 1990.*
Olah, *Friedel–Crafts and Related Reactions*, Interscience Publ., New York, London and Sidney, 1963, vol. 1, pp. 1020–1022.
Jones, et al., "Antiestrogens 2. Structure–Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]phenyl]methanone Hydrochloride (LY156758), a Remarkably Effective Estrogen Antagonist with Only Minimal Intrinsic Estrogenicity," *J. Med. Chem.*, 27, 1057–1066 (1984).
Pinney and Katzenellenbogen, "Synthesis of a Tetrafluoro–Substituted Aryl Azide and Its Protio Analogue as Photoaffinity Labeling Reagents for the Estrogen Receptor," *J. Org. Chem.*, 56, 3125–3133 (1991).
Cheronis, Semimicro Experimental Organic Chemistry, 31–42 (J. de Graff, 1958).
Wagner and Zook, Synthetic Organic Chemistry, 171–172 (John Wiley & Sons, 1953).
Jackson, et al, "Cleavage of 12–Alkylbenzo[a]phenothiazines with Lithium in Tetrahydrofuran: a Dealkylation–Desulphurization Reaction," *J. Chem. Soc.* (C), 1728–1729 (1969).
Kametani, et al, "A Novel Cleavage of Aryl Benzyl Ethers and Allyl Aryl Ethers by Sodium Bis(2–methoxyethoxy)aluminum Hydride. An Alternative Syntheis of Pentazocine," *J. Org. Chem.*, 41 (15), 2545–2548 (1976).

* cited by examiner

*Primary Examiner*—Ceila Chang
(74) *Attorney, Agent, or Firm*—Gilbert T. Voy; James P. Leeds

(57) ABSTRACT

The present invention is directed to chemical processes for preparing 2-aryl-6-hydroxy-3-[4-(2-aminoethoxy)benzoyl]benzo[b]-thiophenes. The present invention is also directed to crystalline solvates and a non-solvated crystalline form of 6-hydroxy-2-(4-hydroxyphenyl)-3-[4-(2-piperidinoethoxy)benzoyl]-benzo[b]thiophene hydrochloride, as well as processes for their preparation.

10 Claims, No Drawings

SYNTHESIS OF 3-[4-(2-AMINOETHOXY)-BENZOYL]-2-ARYL-6-HYDROXYBENZO[B]THIOPHENES

This application is a division of application Ser. No. 08/427,914 filed on Apr. 26, 1995, now abandoned which is a continuation-in-part of application Ser. No. 08/308,325 filed on Sep. 19, 1994 now U.S. Pat. No. 5,629,425.

BACKGROUND OF THE INVENTION

The present invention is directed to chemical processes for preparing 2-aryl-6-hydroxy-3-[4-(2-aminoethoxy)benzoyl]benzo[b]-thiophenes. The synthesis of aromatic ketones was reviewed by Gore in Olah, Friedel-Crafts and Related Reactions, Volume 3, Part 1, Chapter XXXI (1964). Generally, an acyl component and an aromatic substrate are reacted in the presence of a Lewis acid catalyst to produce the aromatic ketone. Suitable Lewis acid catalysts for this type of reaction include metal halides such as aluminum chloride, aluminum bromide, ferric chloride, ferric bromide, and boron trifluoride. See, Olah, Friedel-Crafts and Related Reactions, Volume 1, Chapters II, III, and IV (1963).

The compounds prepared by the present processes were first described in U.S. Pat. No. 4,133,814. This patent described a number of processes for preparing the compounds, including the acylation of suitably protected 2-arylbenzothiophenes. This patent taught the use of phenacyl, halophenacyl, and alkyl protecting groups for the phenolic hydroxyl groups. The alkyl protecting groups were removed by treating the phenolic ethers with pyridine hydrochloride. This patent also taught that the phenolic methyl ethers could be cleaved without affecting the 3-aroylalkoxy group by reacting with boron tribromide; however, the yield of the 3-aroylalkoxy-substituted compound was low.

The process described in U.S. Pat. No. 4,358,593 used particularly advantageous protecting groups for preparing 6-hydroxy-2-(4-hydroxyphenyl)-3-[4-(2-aminoethoxy)benzoyl]-benzo[b]thiophenes. These advantageous protecting groups are acetyl, substituted acetyl, benzoyl, alkylsulfonyl, and arylsulfonyl groups. This patent taught the use of classical Friedel-Crafts catalysts in the acylation of the protected 2-(4-hydroxyphenyl)-6-hydroxybenzo[b]thiophene, including metal halides such as aluminum chloride, aluminum bromide, zinc chloride, boron trifluoride, boron tribromide, titanium tetra-chloride, titanium tetrabromide, stannic chloride, stannic bromide, bismuth trichloride, and ferric chloride. Subsequent to acylation, the protecting group was generally removed under basic conditions.

A particularly useful compound from this series of 2-aryl-3-[4-(2-aminoethoxy)benzoyl]benzo[b]thiophenes is 6-hydroxy-2-(4-hydroxyphenyl)-3-[4-(2-piperidinoethoxy)benzoyl]benzo[b]-thiophene. This compound, as well as methods for its preparation, was first described in U.S. Pat. No. 4,418,068. This compound is a nonsteroidal antiestrogen, useful for alleviating an estrogen-dependent pathological condition of an endocrine target organ.

An improved process for the synthesis of 6-hydroxy-2-(4-hydroxyphenyl)-3-[4-(2-aminoethoxy)benzoyl]benzo[b]thiophenes was described in U.S. Pat. No. 4,380,635. These compounds were prepared by Friedel-Crafts acylation, using aluminum chloride as the catalyst, of a di-O-methyl-protected benzo[b]-thiophene. The intermediate acylation product was demethylated by treating the acylation reaction mixture with a sulfur compound, such as methanethiol, ethanethiol, diethyl sulfide, and methionine. The product of this reaction generally contains aluminum salts and various thioester by-products, which are difficult to remove from the benzothiophene. Also, the product has an unpleasant residual thiol or sulfide odor.

Boron halides, such as boron trichloride and boron tribromide, are useful for the cleavage of arylmethyl ethers. See Bahtt and Kulkarni, *Synthesis*, 249–282 (1983). Boron tribromide has previously been used to cleave arylmethyl ethers in benzothiophene compounds. See German Patent No. DE 4117512 A1.

SUMMARY OF THE INVENTION

The present invention is directed to efficient syntheses of 2-aryl-6-hydroxy-3-[4-(2-aminoethoxy)benzoyl]benzo[b]thiophenes which comprises acylating a suitably protected starting compound, and dealkylating the protected phenolic group(s) to provide the desired product. In accordance with the preferred aspect of the present invention, the acylation and dealkylation steps are performed successively in a single reaction vessel. More specifically, the present invention is directed to a process for preparing a crystalline solvate of a compound of the formula

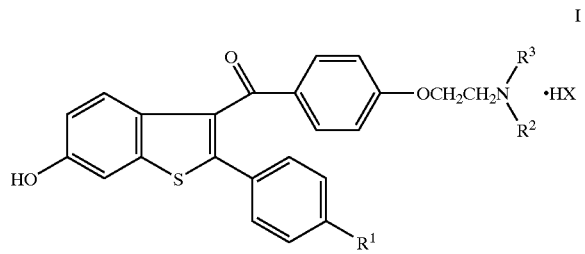

I wherein:

$R^1$ is hydrogen or hydroxyl;

$R^2$ and $R^3$ are independently $C_1$–$C_4$ alkyl, or $R^2$ and $R^3$ together with the adjacent nitrogen atom form a heterocyclic ring selected from the group consisting of pyrrolidino, piperidino, hexamethyleneimino, and morpholino; and HX is HCl or HBr; comprising the steps of:

(a) acylating a benzothiophene of the formula

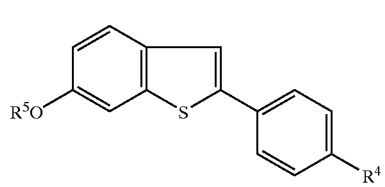

II wherein:
R[4] is hydrogen or $C_1$–$C_4$ alkoxy, and
R[5] is $C_1$–$C_4$ alkyl,
with an acylating agent of the formula

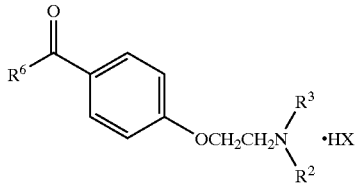

III wherein:
R[6] is chloro, bromo, or hydroxyl, and
HX, R[2], and R[3] are as defined above,
in the presence of BX'$_3$, wherein X' is chloro or bromo;

(b) dealkylating one or more phenolic groups by reacting with additional BX'$_3$, wherein X' is as defined above; and (c) isolating the crystalline solvate.

A second aspect of the present invention is directed to a process for preparing a compound of the formula

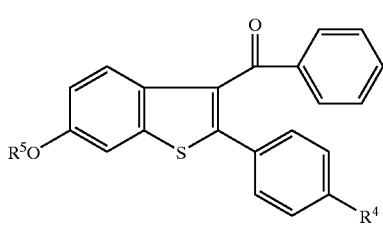

IV or the hydrochloride or hydrobromide salt thereof, wherein:

R[4] is hydrogen or $C_1$–$C_4$ alkoxy,

R[5] is $C_1$–$C_4$ alkyl, and

R[2] and R[3] are independently $C_1$–$C_4$ alkyl, or R[2] and R[3] together with the adjacent nitrogen atom form a heterocyclic ring selected from the group consisting of pyrrolidino, piperidino, hexamethyleneimino, and morpholino;

comprising acylating a benzothiophene of the formula

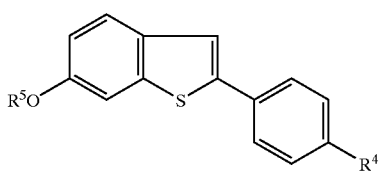

II wherein:
R[4] is hydrogen or $C_1$–$C_4$ alkoxy, and
R[5] is $C_1$–$C_4$ alkyl,
with an acylating agent of the formula

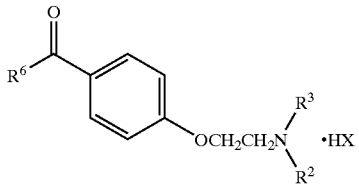

III wherein:
R[6] is chloro, bromo, or hydroxyl;
R[2] and R[3] are independently $C_1$–$C_4$ alkyl, or R[2] and R[3] together with the adjacent nitrogen atom form a heterocyclic ring selected from the group consisting of pyrrolidino, piperidino, hexamethyleneimino, and morpholino; and
HX is HCl or HBr;
in the presence of BX'$_3$, wherein X' is chloro or bromo.

A third aspect of the present invention is directed to a second process for preparing a crystalline solvate of a compound of the formula

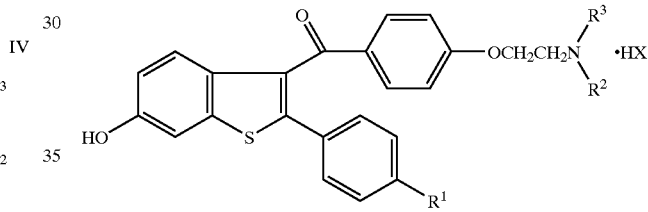

I wherein:
R[1] is hydrogen or hydroxyl;
R[2] and R[3] are independently $C_1$–$C_4$ alkyl, or R[2] and R[3] together with the adjacent nitrogen atom form a heterocyclic ring selected from the group consisting of pyrrolidino, piperidino, hexamethyleneimino, and morpholino; and
HX is HCl or HBr;
comprising dealkylating one or more phenolic groups of a compound of the formula

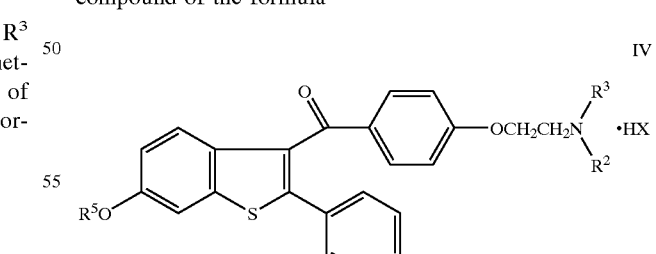

IV

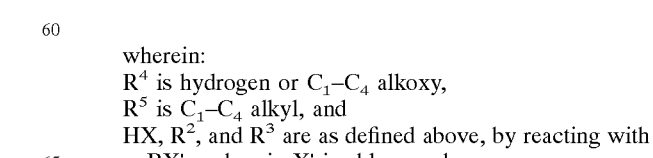

wherein:
R[4] is hydrogen or $C_1$–$C_4$ alkoxy,
R[5] is $C_1$–$C_4$ alkyl, and
HX, R[2], and R[3] are as defined above, by reacting with BX'$_3$, wherein X' is chloro or bromo.

Further aspects of the present invention are crystalline solvates of 6-hydroxy-2-(4-hydroxyphenyl)-3-[4-( 2-piperidino-ethoxy)benzoyl]benzo[b]thiophene hydrochloride and an unsolvated crystalline form of 6-hydroxy-2-(4-hydroxyphenyl)-3-[4-(2-piperidinoethoxy)benzoyl]benzo[b]thiophene hydrochloride, as well as processes for their preparation.

DETAILED DESCRIPTION OF THE INVENTION

In the above formula, the term "$C_1$–$C_4$ alkyl" represents a straight alkyl chain having from 1 to 4 carbon atoms. Typical $C_1$–$C_4$ alkyl groups include methyl, ethyl, n-propyl, and n-butyl. The term "$C_1$–$C_4$ alkoxy" represents groups such as methoxy, ethoxy, n-propoxy, and n-butoxy. The preferred $C_1$–$C_4$ alkoxy group is methoxy.

The term "molar equivalents", as used herein, refers to the number of moles of the boron trihalide reagent in relation to the number of moles of the starting benzothiophene compound.

For example, three millimoles of boron trichloride reacted with one millimole of the benzothiophene compound would represent three molar equivalents of boron trichloride.

The term "solvate" represents an aggregate that comprises one or more molecules of the solute, such as a formula I compound, with a molecule of solvent. Representative solvates are formed with methylene chloride, 1,2-dichloroethane, chloroform, and 1,2,3-trichloropropane.

The term "substantially free from chlorobenezene", as used herein in reference to the non-solvated crystalline 6-hydroxy-2-(4-hydroxyphenyl)-3-[4-(2-piperidinoethoxy)benzoyl]benzo[b]-thiophene hydrochloride, represents a compound containing less than 5% of chlorobenzene calculated on a weight basis (w/w). Preferably, the amount of chlorobenzene is less than 2%, more preferably less than 1%. Most preferably, the amount of chlorobenzene is less than 0.6%.

The term "substantially free from aluminum salts or organoaluminum impurities", as used herein in reference to the non-solvated crystalline 6-hydroxyl-2-(4-hydroxyphenyl)-3-[4-(2-piperidinoethoxy)benzoyl]benzo[b]thiophene hydrochloride, represents a crystalline compound containing less than 5% of a combination of aluminum salts or organoaluminum impurities and other impurities. Preferably, the amount of aluminum salts or organoaluminum impurities is less than 2%, more preferably less than 1%. Representative aluminum salts include, but are not limited to, aluminum hydroxide, aluminum oxides, and hydrated forms thereof. Representative organoaluminum impurities include, but are not limited to, aluminum alkoxides, aluminum(III) complexed to the formula I and IV compounds, and thioaluminates.

The term "substantially odor free", as used herein in reference to the non-solvated crystalline 6-hydroxy-2-(4-hydroxyphenyl)-3-[4-(2-piperidinoethoxy)benzoyl]benzo[b]-thiophene hydrochloride, represents a compound containing less than 3% of mercaptan or sulfide impurities. Preferably, the amount of mercaptan or sulfide impurities is less than 2%, more preferably less than 1%. Representative mercaptan or sulfide impurities include, but are not limited to, $C_1$–$C_6$ alkylthiols (such as ethanethiol and propanethiol) and methyl $C_1$–$C_6$ alkyl sulfides (such as methyl propyl sulfide and ethyl methyl sulfide).

The process of the present invention is useful for the synthesis of a series of compounds having antiestrogenic and antiandrogenic activity. See U.S. Pat. Nos. 4,418,068 and 4,133,814. Representative Formula I compounds, the products of the processes of this invention, include the following compounds: 6-hydroxy-2-phenyl-3-[4-(2-dimethylaminoethoxy)-benzoyl]benzo[b]thiophene, 6-hydroxy-2-(4-hydroxyphenyl)-3-[4-(2-dimethylaminoethoxy)benzoyl]benzo[b]thiophene, 6-hydroxy-2-phenyl-3-[4-(2-diethylaminoethoxy)benzoyl]benzo[b]thiophene, 6-hydroxy-2-(4-hydroxyphenyl)-3-[4-(2-diethylaminoethoxy)-benzoyl]benzo[b]thiophene, 6-hydroxy-2-phenyl-3-[4-(2-diisopropylaminoethoxy)benzoyl]benzo[b]thiophene, 6-hydroxy-2-(4-hydroxyphenyl)-3-[4-(2-diisopropylaminoethoxy)benzoyl]benzo-[b]thiophene, 6-hydroxy-2-phenyl-3-[4-(2-di-n-butylaminoethoxy)-benzoyl]benzo[b]thiophene, 6-hydroxy-2-(4-hydroxyphenyl)-3-[4-(2-di-n-butylaminoethoxy)benzoyl]benzo[b]thiophene, 6-hydroxy-2-phenyl-3-[4-(2-pyrrolidinoethoxy)benzoyl]benzo[b]thiophene, 6-hydroxy-2-(4-hydroxyphenyl)-3-[4-(2-pyrrolidinoethoxy)benzoyl]-benzo[b]thiophene, 6-hydroxy-2-phenyl-3-[4-(2-piperidinoethoxy)-benzoyl]benzo[b]thiophene, 6-hydroxy-2-(4-hydroxyphenyl)-3-[4-(2-piperidinoethoxy)benzoyl]benzo[b]thiophene, 6-hydroxy-2-phenyl-3-[4-(2-hexamethyleneiminoethoxy)benzoyl]benzo[b]-thiophene, 6-hydroxy-2-(4-hydroxyphenyl)-3-[4-(2-hexamethyleneiminoethoxy)benzoyl]benzo[b]thiophene, 6-hydroxy-2-phenyl-3-[4-(2-morpholinoethoxy)benzoyl]benzo[b]thiophene, 6-hydroxy-2-(4-hydroxyphenyl)-3-[4-(2-morpholinoethoxy)benzoyl]benzo[b]-thiophene.

The preferred products of the claimed processes are the Formula I compounds wherein $R^1$ is hydroxyl, and $R^2$ and $R^3$ together with the adjacent nitrogen atom form a pyrrolidino, piperidino, or hexamethyleneimino group. Representative products from this preferred group include 6-hydroxy-2-(4-hydroxyphenyl)-3-[4-(2-pyrrolidinoethoxy)benzoyl]benzo[b]-thiophene, 6-hydroxy-2-(4-hydroxyphenyl)-3-[4-(2-piperidino-ethoxy)benzoyl]benzo[b]thiophene, and 6-hydroxy-2-(4-hydroxy-phenyl)-3-[4-(2-hexamethyleneiminoethoxy)benzoyl]benzo[b]-thiophene. More preferably, the products of the present invention are the Formula I compounds wherein $R^2$ and $R^3$ together with the adjacent nitrogen atom form a pyrrolidino or piperidino group. Representative products from this more preferred group include 6-hydroxy-2-(4-hydroxyphenyl)-3-[4-(2-pyrrolidino-ethoxy)benzoyl]benzo[b]thiophene and 6-hydroxy-2-(4-hydroxy-phenyl)-3-[4-(2-piperidinoethoxy)benzoyl]benzo[b]thiophene. Most preferably, the product of the present invention is the Formula I compound wherein $R^1$ is hydroxyl, and $R^2$ and $R^3$ together with the adjacent nitrogen atom form a piperidino group. This most preferred product is 6-hydroxy-2-(4-hydroxyphenyl)-3-[4-(2-piperidinoethoxy)benzoyl]benzo[b]-thiophene.

The present invention has several advantages over the prior art processes described above. The processes of the present invention use boron tribromide or boron trichloride as the acylation catalyst in place of aluminum chloride. Aluminum chloride is difficult to handle, especially on a commercial scale. Also, a large amount of aluminum chloride, typically six equivalents, is required for acylation and dealkylation. Aluminum chloride produces a large amount of aluminum by-products, which are insoluble in the work-up solvents and difficult to remove from the pharmaceutically active 2-aryl-6-hydroxy-3-[4-(2-aminoethoxy)benzoyl]benzo[b]thiophenes. The aluminum chloride-catalyzed reactions are generally a heterogeneous mixture. The processes of the present invention are homogeneous, and the boron by-products are soluble in the work-up solvents. Further, the aluminum chloride-catalyzed dealkylation required the addition of a mercaptan or a sulfide for cleavage of the alkyl aryl ethers producing dialkyl sulfides, which exhibit offensive odors. These mercaptans or sulfides are removable by recrystallization; however, this produces a recrystallization solvent with the odorous impurities. The processes of the present invention eliminate the use of aluminum and the use of odorous mercaptans and sulfides. Typically, the art processes produced a high quantity of related substances and high levels of residual aluminum salts in the final product. Representative related substances include 6-hydroxy-2-(4-methoxyphenyl)-3-[4-(2-piperidinoethoxy)benzoyl]benzo[b]-thiophene, 2-(4-hydroxyphenyl)-6-methoxy-3-[4-(2-piperidino-ethoxy)benzoyl]benzo[b]thiophene, 6-hydroxy-3-(4-hydroxy-benzoyl)-2-(4-hydroxyphenyl)benzo[b]thiophene, propyl 4-(2-piperidinoethoxy)thiobenzoate, methyl 4-(2-piperidinoethoxy)-benzoate, 6-hydroxy-2-(4-hydroxyphenyl)-3-[4-(2-piperidino-ethoxy)benzoyl]-5-[4-(2-piperidinoethoxy)benzoyl]benzo[b]-thiophene, and 6-hydroxy-2-(4-hydroxyphenyl)-3-[4-(2-piperidino-ethoxy)benzoyl]-7-[4-(2-piperidinoethoxy)benzoyl]benzo[b]-thiophene. The boron by-products are easily removed from the final product. Also, the present process avoids the disposal of aluminum waste. When the reaction is carried out in 1,2-dichloroethane, the reactions are homogeneous allowing the use of higher concentrations, and produce crystalline solvates that are readily isolated.

The Formula II and III compounds, the starting materials for the present invention, are prepared using standard synthetic organic methods. The Formula II starting compound can be readily obtained by a synthesis which is exemplified below in Preparation I and outlined in Scheme I.

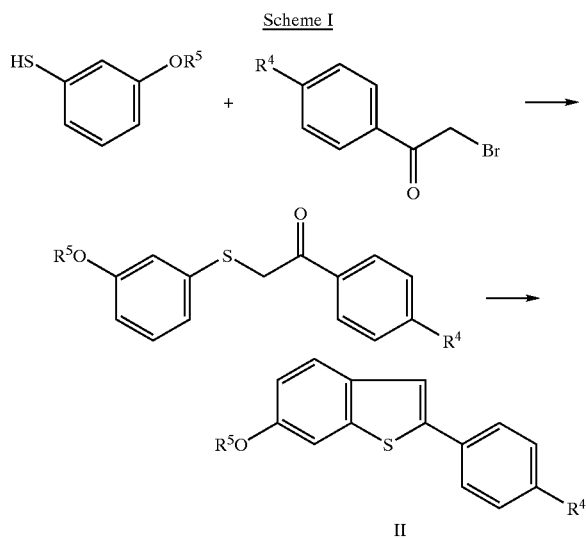

Scheme I

The Formula II compounds, wherein $R^4$ and $R^5$ are as defined above, can be prepared by first reacting a 3-alkoxybenzenethiol with phenacyl or 4'-alkoxyphenacyl bromide in the presence of a strong base. Suitable bases for this transformation include, but are not limited to, potassium hydroxide and sodium hydroxide. The reaction is typically carried out in ethanol or a mixture of water and ethanol at a temperature of about 0° C. to about 50° C. The next step is cyclization of the arylphenacyl-sulfide. The cyclization is conveniently carried out by heating the arylphenacylsulfide in polyphosphoric acid. The cyclization is typically carried out at a temperature of about 80° C. to about 120° C., preferably between 85° C. and 90° C. The Formula II benzo-thiophene is typically purified by recrystallization.

For example, when $R^4$ is methoxy and $R^5$ is methyl, the formula II compound may be recrystallized from ethyl acetate.

The acylating agent for the present process, a Formula III compound, can be prepared as shown in Scheme II, wherein the variables $R^2$, $R^3$, $R^6$, and HX are as defined above and R is $C_1$–$C_4$ alkyl.

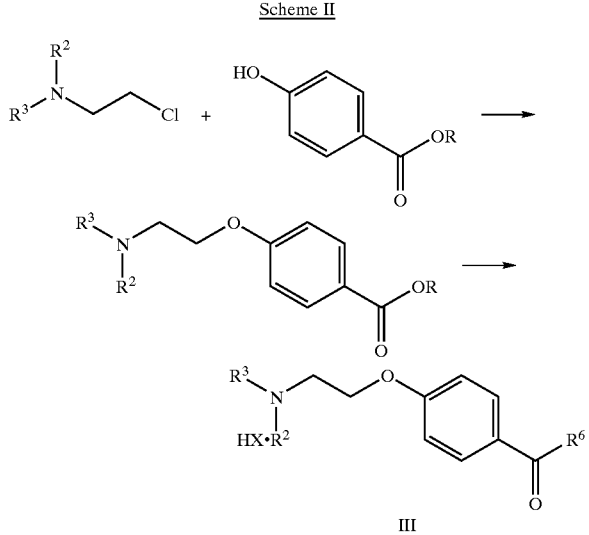

Scheme II

Generally, a $C_1$–$C_4$ alkyl 4-hydroxybenzoate is alkylated with a chloroethylamine in the presence of an inorganic base and the ester group hydrolized to produce the Formula III compounds, wherein $R^6$ is hydroxyl. Examples of chloroethylamines that are useful for preparing the Formula I compounds are 1-(2-chloroethyl)piperidine, 4-(2-chloroethyl)morpholine, and 1-(2-chloroethyl)pyrrolidine. Suitable inorganic bases for this alkylation include potassium carbonate and sodium carbonate. Suitable solvents for this alkylation are non-reactive polar organic solvents such as methyl ethyl ketone and dimethylformamide. The ester is hydrolized using standard synthetic methods, such as by reaction of the alkylated intermediate with an aqueous acid or base. For example, the ethyl ester is readily hydrolyzed by reaction with 5N sodium hydroxide in a water miscible organic solvent, such as methanol. Acidification of the reaction with concentrated hydrochloric acid produces the Formula III compound, wherein $R^6$ is hydroxyl, as the hydrochloride salt.

The Formula III compounds, wherein $R^6$ is chloro or bromo, are prepared by halogenating the Formula III compounds wherein $R^6$ is hydroxyl. Suitable halogenating agents include oxalyl chloride, thionyl chloride, thionyl bromide, phosphorous tribromide, triphosgene, and phosgene. Preferably, $R^6$ is chloro. Suitable solvents for this reaction include methylene chloride, 1,2-dichlorobenzene, chlorobenzene, and 1,2-dichloro-ethane. Preferably, the halogenation reaction is carried out in the same solvent as the subsequent acylation reaction. A catalytic amount of dimethylformamide, from about 0.05 to about 0.25 equivalents, is added to the chlorination reaction. When the reaction is carried out in 1,2-dichloroethane, the reaction is complete after about 2 to 5 hours at about 47° C. The Formula III compounds, wherein $R^6$ is chloro, may be stored as a solid, or as a solution or mixture in methylene chloride, chlorobenzene, 1,2-dichlorobenzene, or 1,2-dichloroethane. Preferably, the chlorination reaction and acylation reaction are carried out successively in the same reaction vessel.

The 2-aryl-6-hydroxy-3-[4-(2-aminoethoxy)benzoyl[b]-thiophenes can be prepared by acylation and subsequent dealkylation of the phenolic groups in two distinct steps, or sequentially in a "one-pot" reaction. The step-wise synthesis is described in the following paragraphs. The acylated benzothiophene intermediate, a Formula IV compound, is prepared as shown in Scheme III, wherein $R^2$, $R^3$, $R^4$, $R^5$, $R^6$, and HX are as defined above.

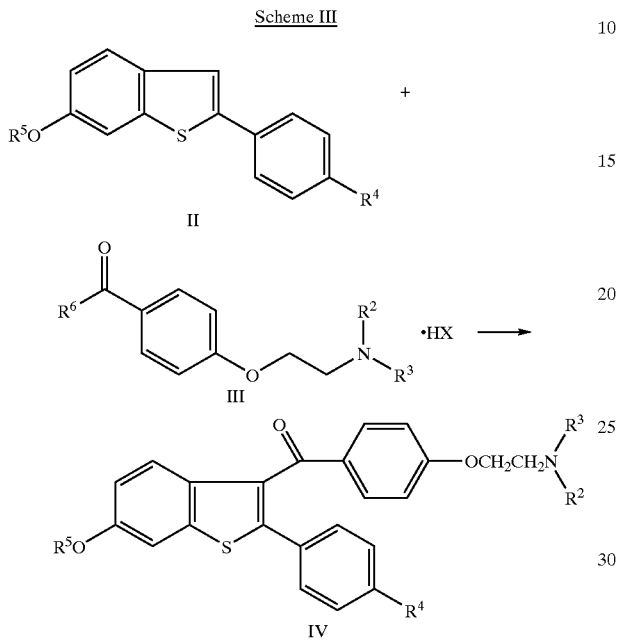

Scheme III

Generally, benzothiophene intermediate II is acylated with a Formula III compound, using boron trichloride or boron tribromide as the acylation catalyst. The reaction is carried out in an organic solvent, such as chlorobenzene, methylene chloride, 1,2-dichloroethane, 1,2-dichlorobenzene, bromobenzene, chloroform, 1,1,2,2-tetrachloroethane, 1,2,3-trichloropropane, and fluorobenzene. Preferably, the acylation is carried out in methylene chloride, chlorobenzene, or 1,2-dichloroethane. Most preferably, the acylation step is carried out in methylene chloride. The rate of acylation of the Formula II compound and the rate of dealkylation of the phenolic ethers of the Formula II and IV compounds varies with the choice of solvent, temperature of reaction, and choice of boron trihalide. Because the Formula II compounds having one or more unprotected phenolic groups will not acylate readily under these conditions, the amount of dealkylation must be minimized. Because boron tribromide is more preferred for dealkylation of phenolic ethers, the preferred boron trihalide for catalyzing acylation is boron trichloride. For boron trichloride-catalyzed reactions in methylene chloride, the acylation reaction can be performed at room temperature, with minimal dealkylation of the Formula II and IV compounds. In other solvents, the acylation reaction is carried out at lower temperatures, such as –10° C. to 10° C., to minimize the amount of dealkylation of the reaction starting material and product. When $R^6$ is chloro, at least 2 molar equivalents of the boron trihalide reagent are required for acylation. When the benzoic acid is used as an acylating agent ($R^6$=OH), five equivalents of the boron trihalide are typically used. The Formula IV compound may be isolated as the hydrochloride or hydrobromide salt, or as the free base.

In the step-wise process, the acylated intermediate (Formula IV compound) is dealkylated to produce the Formula I compound as shown in Scheme IV, wherein $R^1$, $R^2$, $R^3$, $R^4$, $R^5$, and HX are as defined above.

Scheme IV

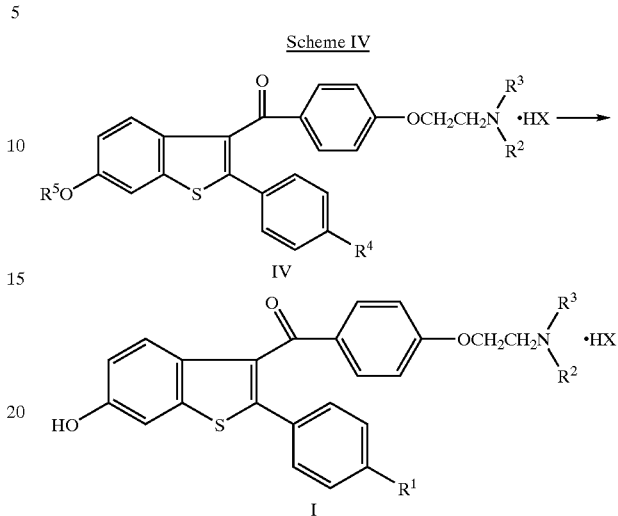

The Formula I compound can be produced by reacting the hydrochloride or hydrobromide salt of the Formula IV compound with boron tribromide or boron trichloride. The preferred boron trihalide for dealkylation is boron tribromide. This dealkylation reaction can be carried out in a variety of organic solvents, such as methylene chloride, chlorobenzene, 1,2-dichloroethane, chloroform, 1,1,2,2-tetrachloroethane, 1,2,3-trichloropropane, 1,2-dichlorobenzene, and fluorobenzene. The preferred solvent is 1,2-dichloroethane. When the acid addition salt is used as a starting material, the amount of by-product resulting from dealkylation of the aminoethyl group is minimized. When methylene chloride is used as the solvent and the boron reagent is boron trichloride, the reaction is generally carried out at a temperature of about 55° C. to about 75° C., producing the Formula I compound with no detectable cleavage of the aminoethyl group. In other solvents, such as chloroform, 1,2-dichloro-ethane, chlorobenzene, 1,2-dichlorobenzene, and fluorobenzene, the dealkylation occurs readily at ambient temperatures. For example, when 1,2-dichloroethane is the solvent, the reaction is generally carried out at 25° C. to 35° C. with no detectable cleavage of the aminoethyl group. At least four equivalents of the boron trihalide reagent are typically used for complete reaction within a reasonable time.

Preferably, the Formula I compounds are prepared by a "one-pot" synthesis from the Formula II and III compounds as shown in Scheme V, wherein $R^1$, $R^2$, $R^3$, $R^4$, $R^5$, $R^6$, and HX are as defined above.

Scheme V

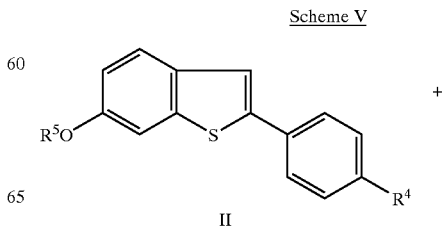

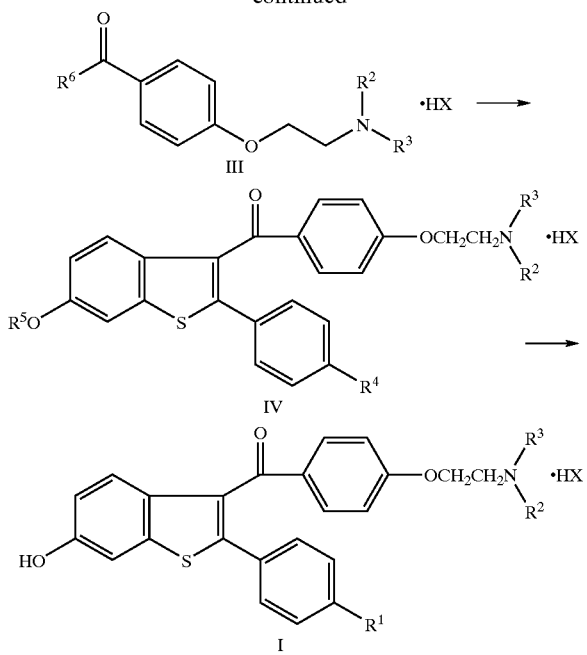

The benzothiophene Formula II compound is acylated with the Formula III compound in the presence of boron trichloride or boron tribromide; boron trichloride is preferred for the "one-pot" process. The reaction can be carried out in a variety of organic solvents, such as chloroform, methylene chloride, 1,2-dichloroethane, 1,2,3-trichloropropane, 1,1,2,2-tetrachloro-ethane, 1,2-dichlorobenzene, chlorobenzene, and fluorobenzene. The preferred solvent for this synthesis is 1,2-dichloroethane. The reaction is carried out at a temperature of about −10° C. to about 25° C., preferably at 0° C. The reaction is best carried out at a concentration of the benzothiophene Formula II compound of about 0.2 M to about 1.0 M. The acylation reaction is generally complete after about two hours to about eight hours.

The acylated benzothiophene, the Formula IV compound, is converted to a Formula I compound without isolation. This conversion is performed by adding additional boron trihalide and heating the reaction mixture. Preferably, two to five molar equivalents of boron trichloride are added to the reaction mixture, most preferably three molar equivalents. This reaction is carried out at a temperature of about 25° C. to about 40° C., preferably at 35° C. The reaction is generally complete after about 4 to 48 hours. The acylation/dealkylation reaction is quenched with an alcohol or a mixture of alcohols. Suitable alcohols for use in quenching the reaction include methanol, ethanol, and isopropanol. Preferably, the acylation/dealkylation reaction mixture is added to a 95:5 mixture of ethanol and methanol (3A). The 3A ethanol can be at room temperature or heated to reflux, preferably at reflux. When the quench is performed in this manner, the Formula I compound conveniently crystallizes from the resulting alcoholic mixture. Generally, 1.25–3.75 mL of alcohol per millimole of the benzothiophene starting material are used.

The crystalline product of this "one-pot" process, when $BCl_3$ is used, is isolated as the solvate of the hydrochloride salt. These crystalline solvates are obtained under a variety of conditions. The preparation of a solvate of the Formula I compound, wherein $R^1$ is hydroxyl, HX is HCl, and $R^2$ and $R^3$ together with the adjacent nitrogen atom form a piperidino group, was described previously. Jones et al., *J. Med. Chem.*, 27, 1057 (1984). Generally, the form of the product of the present process is determined by choice of acylation/dealkylation solvent, boron trihalide, and work-up conditions.

A particularly useful solvate of the formula I compound is the 1,2-dichloroethane solvate. This solvate is prepared by carrying out the "one-pot" acylation/dealkylation process in 1,2-dichloroethane. When $R^1$ is hydroxyl, $R^2$ and $R^3$ together with the adjacent nitrogen atom form a piperidino group, and HX is HCl, the 1,2-dichloroethane solvate can exist in two distinct forms. One crystalline solvate form, termed crystal form I, is prepared by quenching the boron trichloride-catalyzed acylation/dealkylation reaction with ethanol. Preferably, a mixture of ethanol and methanol (95:5) is used in the preparation of this crystal form. This particular crystal form is characterized by the X-ray diffraction pattern shown in Table 1.

TABLE 1

X-ray Diffraction Pattern for Crystal Form I.

| d-line spacing (Angstroms) | $I/I_o$ (×100) |
|---|---|
| 16.1265 | 3.80 |
| 10.3744 | 8.63 |
| 8.3746 | 5.29 |
| 7.9883 | 36.71 |
| 7.2701 | 5.06 |
| 6.5567 | 70.77 |
| 6.2531 | 6.79 |
| 5.5616 | 24.05 |
| 5.3879 | 100.00 |
| 5.0471 | 89.64 |
| 4.7391 | 85.96 |
| 4.6777 | 39.36 |
| 4.6332 | 62.60 |
| 4.5191 | 77.56 |
| 4.2867 | 36.82 |
| 4.2365 | 41.66 |
| 4.1816 | 49.60 |
| 4.0900 | 11.28 |
| 3.9496 | 11.85 |
| 3.7869 | 36.25 |
| 3.7577 | 56.16 |
| 3.6509 | 40.62 |
| 3.5751 | 15.65 |
| 3.5181 | 21.52 |
| 3.4964 | 18.53 |
| 3.4361 | 33.60 |
| 3.3610 | 6.21 |
| 3.3115 | 4.95 |
| 3.2564 | 7.36 |
| 3.2002 | 3.80 |
| 3.1199 | 15.77 |
| 3.0347 | 14.84 |
| 2.8744 | 9.67 |
| 2.8174 | 10.82 |
| 2.7363 | 11.51 |

The amount of 6-hydroxy-2-(4-hydroxyphenyl)-3-[4-(2-piperidinoethoxy)benzoyl]benzo[b]thiophene hydrochloride present in the crystalline material is about 87.1%, as determined using the high performance liquid chromatography (HPLC) assay described below. The amount of 1,2-dichloroethane present in the crystalline material is about 0.55 molar equivalents, as determined by proton nuclear magnetic resonance spectroscopy.

A large, analytically pure single crystal of the form I 1,2-dichloroethane solvate was prepared for single crystal X-ray analysis. This single crystal was prepared by placing a saturated methanolic solution of 6-hydroxy-2-(4- hydroxyphenyl)-3-[4-(2-piperidinoethoxy)benzoyl]benzo[b]thiophene hydrochloride in an atmosphere saturated with 1,2-dichloroethane (see Example 8). A total of 8419 reflections with 2θ less than 116° were collected, and used to solve the structure. The X-ray structure clearly shows that the crystalline material is a 1,2-dichloroethane solvate having a 1:2 ratio of solvent to solute molecules. The theoretical X-ray powder diffraction pattern spectrum, calculated from the single crystal X-ray data, is identical to that listed in Table 1, indicating that both solvates are identical.

A second crystalline solvate form, termed crystal form II, is similar to crystal form I. This second form is prepared by quenching the boron trichloride-catalyzed acylation/dealkylation reaction carried out in 1,2-dichloroethane with methanol. Alternatively, the boron trichloride-catalyzed acylation/dealkylation reaction using 1,2,3-trichloropropane as the solvent, produces a 1,2,3-trichloropropane solvate of this form. This particular crystal form is characterized by the X-ray diffraction pattern shown in Table 2.

TABLE 2

X-ray Diffraction Pattern for Crystal Form II.

| d-line spacing (Angstroms) | $I/I_o$ (×100) |
|---|---|
| 10.4311 | 22.64 |
| 8.9173 | 10.73 |
| 8.4765 | 5.31 |
| 8.0095 | 50.39 |
| 7.3068 | 4.23 |
| 6.6094 | 79.23 |
| 5.6196 | 22.34 |
| 5.4223 | 89.86 |
| 5.1959 | 11.81 |
| 5.0746 | 74.90 |
| 4.8017 | 100.00 |
| 4.7262 | 57.97 |
| 4.6569 | 53.35 |
| 4.5378 | 96.75 |
| 4.4376 | 10.83 |
| 4.3397 | 56.89 |
| 4.2782 | 48.23 |
| 4.2129 | 40.94 |
| 4.1037 | 12.80 |
| 3.9880 | 14.76 |
| 3.8863 | 8.17 |
| 3.7999 | 42.13 |
| 3.7662 | 57.09 |
| 3.6738 | 38.58 |
| 3.5701 | 18.50 |
| 3.5393 | 19.00 |
| 3.4622 | 39.57 |
| 3.3867 | 5.02 |
| 3.3321 | 4.33 |
| 3.2686 | 6.79 |
| 3.1535 | 14.86 |
| 3.0450 | 13.58 |
| 2.9028 | 12.30 |
| 2.8302 | 19.59 |
| 2.7544 | 12.30 |
| 2.6366 | 6.89 |

The amount of 6-hydroxy-2-(4-hydroxyphenyl)-3-[4-(2-piperidinoethoxy)benzoyl]benzo[b]thiophene hydrochloride present in the crystalline material is about 86.8%. The amount of 1,2-dichloroethane present in the crystalline material is about 6.5%, as determined by gas chromatography.

The formula I compounds form a variety of distinct solvates with aromatic solvents. Copending U.S. application Ser. No. 08/308,322 (X-9444), filed Sep. 19, 1994, describes a number of aromatic solvates of 6-hydroxy-2-(4-hydroxyphenyl)-3-[4-(2-piperidinoethoxy)benzoyl]benzo[b]thiophene hydrochloride. A useful aromatic solvate of this compound is the chlorobenzene solvate, which exists in a distinct form termed crystal form III. This particular crystal form is characterized by the X-ray diffraction pattern shown in Table 3.

TABLE 3

X-ray Diffraction Pattern for Crystal Form III.

| d-line spacing (Angstroms) | $I/I_o$ (×100) |
|---|---|
| 14.3518 | 7.24 |
| 10.3335 | 6.17 |
| 8.8305 | 4.29 |
| 7.9475 | 38.16 |
| 6.5904 | 64.25 |
| 6.2848 | 6.52 |
| 5.6048 | 28.06 |
| 5.4107 | 100.00 |
| 5.1544 | 11.26 |
| 5.0493 | 53.26 |
| 5.0224 | 46.11 |
| 4.8330 | 76.94 |
| 4.7694 | 34.23 |
| 4.6461 | 50.22 |
| 4.5754 | 38.61 |
| 4.4953 | 72.65 |
| 4.3531 | 49.15 |
| 4.2940 | 41.64 |
| 4.2425 | 35.75 |
| 4.1856 | 21.63 |
| 4.1338 | 9.47 |
| 4.0793 | 12.69 |
| 3.9960 | 18.50 |
| 3.9037 | 9.03 |
| 3.7854 | 40.39 |
| 3.7521 | 54.16 |
| 3.6787 | 28.60 |
| 3.6509 | 17.96 |
| 3.5444 | 31.72 |
| 3.4679 | 41.55 |
| 3.3899 | 7.69 |
| 3.3101 | 5.72 |
| 3.2561 | 7.42 |
| 3.1784 | 15.19 |
| 3.0445 | 11.17 |
| 3.0146 | 8.94 |
| 2.9160 | 11.89 |
| 2.8217 | 18.23 |
| 2.7500 | 12.06 |
| 2.6436 | 9.65 |
| 2.6156 | 6.97 |

The amount of 6-hydroxy-2-(4-hydroxyphenyl)-3-[4-(2-piperidinoethoxy)benzoyl]benzo[b]thiophene hydrochloride present in the crystalline material is about 78.6%. The amount of chlorobenzene present in the crystalline material is about 12.3%, as determined by HPLC.

A fourth crystalline solvated form is termed crystal form IV. This particular form is prepared by the boron trichloride-catalyzed acylation/dealkylation process using methylene chloride or chloroform as the solvent. This particular crystal form is characterized by the X-ray diffraction pattern shown in Table 4.

TABLE 4

X-ray Diffraction Pattern for Crystal Form IV.

| d-line spacing (Angstroms) | $I/I_o$ (×100) |
|---|---|
| 10.3696 | 14.40 |
| 8.9032 | 10.19 |

TABLE 4-continued

X-ray Diffraction Pattern for Crystal Form IV.

| d-line spacing (Angstroms) | I/I$_o$ (×100) |
|---|---|
| 8.3125 | 7.61 |
| 7.9818 | 41.03 |
| 7.2036 | 7.34 |
| 6.5411 | 74.18 |
| 6.2367 | 6.39 |
| 5.5539 | 20.11 |
| 5.3689 | 100.00 |
| 5.0272 | 95.92 |
| 4.7085 | 89.13 |
| 4.6406 | 73.37 |
| 4.6199 | 77.58 |
| 4.5347 | 69.70 |
| 4.4818 | 49.86 |
| 4.2589 | 47.69 |
| 4.2067 | 44.43 |
| 4.1659 | 44.16 |
| 4.0957 | 11.96 |
| 3.9347 | 11.28 |
| 3.7818 | 40.90 |
| 3.7614 | 53.53 |
| 3.6375 | 36.68 |
| 3.5773 | 20.11 |
| 3.5037 | 25.14 |
| 3.4409 | 32.34 |
| 3.4270 | 39.54 |
| 3.3088 | 12.64 |
| 3.2611 | 9.65 |
| 3.1046 | 12.77 |
| 3.0263 | 17.53 |
| 2.8536 | 8.29 |
| 2.8131 | 12.09 |
| 2.7309 | 8.97 |

The amount of 6-hydroxy-2-(4-hydroxyphenyl)-3-[4-(2-piperidinoethoxy)benzoyl]benzo[b]thiophene hydrochloride present in the crystalline material is about 80.4%, as determined by HPLC analysis. The amount of chloroform present in the crystalline material is about 0.42 molar equivalents, as determined by proton nuclear magnetic resonance spectroscopy.

A preferred crystalline form of 6-hydroxy-2-(4-hydroxyphenyl)-3-[4-(2-piperidinoethoxy)benzoyl]benzo[b]thiophene hydrochloride is a non-solvated crystal form. This particular form is preferred for use in the preparation of pharmaceutical formulations because of the absence of solvent that could affect the patient. This particular crystal form is prepared by recrystallization of the solvated hydrochloride salt produced by the boron trichloride-catalyzed acylation/dealkylation process. Generally, the solvated hydrochloride salt is added to a solution of sodium hydroxide in methanol or a mixture of methanol and water. At least one equivalent of base is used for dissolution and to ensure that the hydrochloride salt is converted to the free base. Activated carbon is optionally added to the resulting solution to facilitate removal of impurities. The mixture is filtered to remove the activated carbon, if present, and any insoluble impurities. The filtrate is optionally extracted with an aliphatic hydrocarbon solvent, such as hexane or heptane, to remove the organic solvent used in the acylation/dealkylation reaction. The extraction step is required when the acylation/dealkylation reaction is carried out in aromatic solvents, such as chlorobenzene, fluorobenzene, bromobenzene, and o-dichlorobenzene. The methanol solution is acidified with hydrochloric acid, such as gaseous or aqueous hydrochloric acid, causing crystallization of 6-hydroxy-2-(4-hydroxyphenyl)-3-[4-(2-piperidinoethoxy) benzoyl]benzo[b]-thiophene as the non-solvated hydrochloride salt. The resulting crystalline slurry is preferably stirred at ambient temperature for about one to about two hours to ensure complete crystallization. The non-solvated crystalline form is isolated by filtration, followed by drying in vacuo. This particular crystal form is characterized by the X-ray diffraction pattern shown in Table 5.

TABLE 5

X-ray Diffraction Pattern for Non-solvated Crystal Form.

| d-line spacing (Angstroms) | I/I$_o$ (×100) |
|---|---|
| 13.3864 | 71.31 |
| 9.3598 | 33.16 |
| 8.4625 | 2.08 |
| 7.3888 | 7.57 |
| 6.9907 | 5.80 |
| 6.6346 | 51.04 |
| 6.1717 | 29.57 |
| 5.9975 | 5.67 |
| 5.9135 | 9.87 |
| 5.6467 | 38.47 |
| 5.4773 | 10.54 |
| 5.2994 | 4.74 |
| 4.8680 | 4.03 |
| 4.7910 | 5.98 |
| 4.6614 | 57.50 |
| 4.5052 | 5.75 |
| 4.3701 | 9.03 |
| 4.2516 | 69.99 |
| 4.2059 | 57.64 |
| 4.1740 | 65.07 |
| 4.0819 | 12.44 |
| 3.9673 | 22.53 |
| 3.9318 | 100.00 |
| 3.8775 | 9.07 |
| 3.7096 | 33.38 |
| 3.6561 | 21.65 |
| 3.5576 | 3.36 |
| 3.5037 | 7.97 |
| 3.4522 | 18.02 |
| 3.4138 | 4.65 |
| 3.2738 | 10.23 |
| 3.1857 | 8.90 |
| 3.1333 | 6.24 |
| 3.0831 | 9.43 |
| 3.0025 | 12.13 |
| 2.9437 | 4.96 |
| 2.8642 | 7.70 |
| 2.7904 | 11.95 |
| 2.7246 | 3.05 |
| 2.6652 | 3.32 |
| 2.5882 | 7.30 |

The amount of 6-hydroxy-2-(4-hydroxyphenyl)-3-[4-(2-piperidinoethoxy)benzoyl]benzo[b]thiophene hydrochloride present in the crystalline material is at least 95%.

This non-solvated crystalline material is more pure than the material produced by the processes described in the above-referenced patents. The present material is free of aluminum impurities, as well as, chlorinated aliphatic hydrocarbon solvents and aromatic solvents. This non-solvated crystalline form is particularly preferred for use in the manufacture of pharmaceutical compositions.

The following examples further illustrate the processes of the present invention. The examples are not intended to be limiting to the scope of the invention in any respect, and should not be so construed. All experiments were run under positive pressure of dry nitrogen. All solvents and reagents were used as obtained. The percentages are generally calculated on a weight (w/w) basis; except for HPLC solvents which are calculated on a volume (v/v) basis. Proton nuclear magnetic resonance ($^1$H NMR) spectra were obtained on a Bruker AC-300 FTNMR spectrometer at 300.135 MHz. Melting points were determined by differential scanning calorimetry (DSC) in a TA Instrument DCS 2920 using a closed cell and a heating rate of 2° C./minute. The X-ray powder diffraction spectra were obtained in a Siemens D5000 X-Ray Powder Diffraktometer, using copper radiation and a Si(Li) detector.

The reactions were generally monitored for completion using high performance liquid chromatography (HPLC). The reaction producing the acid chloride, the Formula III compound wherein $R^6$ is chloro, was monitored using a Zorbax RX-C8 column (25cm×4.6 mm ID, 5 μparticle), eluting with a mixture of 60 mM phosphate ($KH_2PO_4$) and 10 mM octanesulfonate (pH 2.0)/acetonitrile (60:40). The Formula III compound was derivatized with methanol, and analyzed using a methyl ester reference standard. The reaction was monitored by the addition of about 0.3 mL of the acid chloride solution to 1 mL of HPLC grade methanol. The resulting mixture was shaken vigorously and allowed to derivatize. After 30 minutes, acetonitrile (6 mL) was added followed by dilution to 100 mL with the eluent described above.

The acylation, dealkylation, or acylation/dealkylation reactions were also monitored for completion by HPLC. A sample of the reaction mixture was assayed using a Zorbax RX-C8 column (25 cm×4.6 mm ID, 5 μ particle), eluting with a gradient as shown below:

| GRADIENT SOLVENT SYSTEM | | |
| --- | --- | --- |
| Time (min.) | A (%) | B (%) |
| 0 | 60 | 40 |
| 5 | 60 | 40 |
| 10 | 45 | 55 |
| 20 | 38 | 62 |
| 25 | 45 | 55 |
| 32 | 45 | 55 |
| 37 | 60 | 40 |
| 42 | 60 | 40 |

A: 0.05 M $HClO_4$ (pH = 2.0)
B: acetonitrile

The reaction mixture was analyzed by diluting a 0.1 mL to 0.2 mL sample to 50 mL with a 60:40 mixture of A/B. Similarly, the mother liquor of the recrystallizations was sampled in a similar manner.

The amount (percentages) of 6-hydroxy-2-(4-hydroxyphenyl)-3-[4-(2-piperidinoethoxy)benzoyl]benzo[b]thiophene hydrochloride in the crystalline material (potency) was determined by the following method. A sample of the crystalline solid (5 mg) was weighed into a 100-mL volumetric flask, and dissolved in a 70/30 (v/v) mixture of 75 mM potassium phosphate buffer (pH 2.0) and acetonitrile. An aliquot of this solution (10 μL) was assayed by high performance liquid chromatography, using a Zorbax RX-C8 column (25 cm×4.6 mm ID, 5 μ particle) and UV detection (280 nm). The following gradient solvent system was used:

| Gradient Solvent System (Potency) | | |
| --- | --- | --- |
| time (min) | A (%) | B (%) |
| 0 | 70 | 30 |
| 12 | 70 | 30 |
| 14 | 25 | 75 |
| 16 | 70 | 30 |
| 25 | 70 | 30 |

A: 75 mM $KH_2PO_4$ buffer (pH 2.0)
B: acetonitrile

The percentage of 6-hydroxy-2-(4-hydroxyphenyl)-3-[4-(2-piperidinoethoxy)benzoyl]benzo[b]thiophene hydrochloride in the sample was calculated using the peak area, slope (m), and intercept (b) of the calibration curve with the following equation:

$$\% \text{ potency} = \frac{\text{peak area} - b}{m} \times \frac{\text{sample volume (mL)}}{\text{sample weight (mg)}}$$

The amount (percentage) of solvent, such as methanol, ethanol, or 1,2-dichloroethane, present in the crystalline material can be determined by gas chromatography. A sample of the crystalline solid (50 mg) was weighed into a 10-mL volumetric flask, and dissolved in a solution of 2-butanol (0.025 mg/mL) in dimethylsulfoxide. A sample of this solution was analyzed on a gas chromatograph using a DB Wax column (30 m×0.53 mm ID, 1μ particle), with a column flow of 10 mL/min and flame ionization detection. The column temperature was heated from 35° C. to 230° C. over a 12 minute period. The amount of solvent was determined by comparison to the internal standard (2-butanol), using the following formula:

$$\% \text{ solvent} = \frac{C}{D} \times \frac{E}{F} \times \frac{G}{H} \times I$$

wherein:
C=ratio of solvent in sample
D=average ratio of standard for specific solvent
E=average weight of standard
F=weight of sample (mg)
G=volume of sample (10 mL)
H=volume of standard (10,000 mL)
I=purity of standard (%)

Preparation 1

6-Methoxy-2-(4-methoxyphenyl)benzo[b]thiophene

A solution of 3-methoxybenzenethiol (100 grams) and potassium hydroxide (39.1 grams) in water (300 mL) was added to denatured ethanol (750 mL), and the resulting mixture cooled to about 0° C. The cold mixture was treated with 4'-methoxyphenacyl bromide (164 grams) in several small portions. Upon complete addition, the mixture was cooled for an additional ten minutes, then allowed to warm to room temperature. After three hours, the mixture was concentrated in vacuo, and the residue treated with water (200 mL). The resulting mixture was treated with ethyl acetate, and the phases were separated. The organic phase was washed with water (2×), sodium bicarbonate solution (2×), and sodium chloride solution (2×). The organic phase was then dried over magnesium sulfate, filtered, and evaporated to dryness in vacuo to give 202 grams of α-(3-methoxyphenylthio)-4-methoxyacetophenone. This crude product was crystallized from methanol and washed with hexane to give 158 grams. Melting point 53° C.

Polyphosphoric acid (930 grams) was heated to 85° C. and treated with the intermediate product from above (124 grams) in small portions over 30 minutes. Upon complete addition, the resulting mixture was stirred at 90° C. After an additional 45 minutes, the reaction mixture was allowed to cool to room temperature. This mixture was treated with crushed ice while the mixture was cooled in an ice bath. The resulting mixture was treated with water (100 mL) producing a light pink precipitate. The precipitate was isolated by filtration, washed with water and methanol, and dried in vacuo at 40° C. to give 119 grams of 6-methoxy-2-(4-methoxyphenyl)benzo[b]thiophene. This crude product was slurried in hot methanol, filtered, and washed with cold methanol. The resulting solid material was recrystallized from ethyl acetate (4 liters), filtered, washed with hexane, and dried in vacuo to 68 grams of the title compound. Melting point 187–190.5° C.

Preparation 2

Ethyl 4-(2-Piperidinoethoxy)benzoate

A mixture of ethyl 4-hydroxybenzoate (8.31 g), 1-(2-chloroethyl)piperidine monohydrochloride (10.13 g), potassium carbonate (16.59 g), and methyl ethyl ketone (60 mL) was heated to 80° C. After one hour, the mixture was cooled to about 55° C. and treated with additional 1-(2-chloroethyl) piperidine monohydrochloride (0.92 g). The resulting mixture was heated to 80° C. The reaction was monitored by thin layer chromatography (TLC), using silica-gel plates and ethyl acetate/acetonitrile/triethylamine (10:6:1, v/v). Additional portions of 1-(2-chloroethyl)piperidine hydrochloride were added until the starting 4-hydroxybenzoate ester was consumed. Upon complete reaction, the reaction mixture was treated with water (60 mL) and allowed to cool to room temperature. The aqueous layer was discarded and the organic layer concentrated in vacuo at 40° C. and 40 mm Hg. The resulting oil :was used in the next step without further purification.

Preparation 3

4-(2-Piperidinoethoxy)benzoic Acid Hydrochloride

A solution of the compound prepared as described in Preparation 2 (about 13.87 g) in methanol (30 mL) was treated with 5 N sodium hydroxide (15 mL), and heated to 40° C. After 4 ½ hours, water (40 mL) was added. The resulting mixture was cooled to 5–10° C., and concentrated hydrochloric acid (18 mL) was added slowly. The title compound crystallized during acidification. This crystalline product was collected by filtration, and dried in vacuo at 40–50° C. to give 83% yield of the title compound. Melting point 270–271° C.

Preparation 4

4-(2-Piperidinoethoxy)benzoyl Chloride Hydrochloride

A solution of the compound prepared as described in Preparation 3 (30.01 g) and dimethylformamide (2 mL) in methylene chloride (500 mL) was treated with oxalyl chloride. (10.5 mL) over a 30–35 minute period. After stirring for about 18 hours, the reaction was assayed for completion by HPLC analysis. Additional oxalyl chloride may be added to the reaction if the starting carboxylic acid is present. Upon completion, the reaction solution was evaporated to dryness in vacuo. The residue was dissolved in methylene chloride (200 mL), and the resulting solution evaporated to dryness. This dissolution/evaporation procedure was repeated to give the title compound as a solid. The title compound may be stored as a solid or as a 0.2 M solution in methylene chloride (500 mL).

EXAMPLE 1

6-Methoxy-2-(4-methoxyphenyl)-3-[4-(2-piperidinoethoxy)benzoyl]-benzo[b]thiophene Hydrochloride A mixture of the compound prepared as described in Preparation 1 (8.46 grams) and the acid chloride prepared as described in Preparation 4 (10.0 grams) in methylene chloride (350 mL) was cooled to about 20–25° C. The cool mixture was treated with boron trichloride (2.6 mL), and the resulting mixture mechanically stirred. The reaction was monitored by HPLC using the assay described above. After 85 minutes, the in situ HPLC yield based on a 6-methoxy-2-(4-methoxyphenyl)-3-[4-(2-piperidinoethoxy)benzoyl] benzo[b]thiophene standard was 88%.

EXAMPLE 2

6-Hydroxy-2-(4-hydroxyphenyl)-3-[4-(2-piperidinoethoxy)benzoyl]-benzo[b]thiophene Hydrochloride 1,2-Dichloroethane Solvate (Crystal Form I)

A solution of 6-methoxy-2-(4-methoxyphenyl)-3-[4-(2-piperidinoethoxy)benzoyl]benzo[b]thiophene hydrochloride (2.0 g) in 1,2-dichloroethane (20 mL) was treated with boron trichloride (2.0 mL). The resulting mixture was stirred at 35° C. for about 18 hours. A mixture of ethanol and methanol (10 mL, 95:5, 3A) was treated with the reaction mixture from above, causing the alcoholic mixture to reflux. Upon complete addition, the resulting crystalline slurry was stirred at 25° C. After one hour, the crystalline product was filtered, washed with cold ethanol (10 mL), and dried at 40° C. in vacuo to give 1.78 g of the title compound. The X-ray powder diffraction pattern is identical to that reported in Table 1. Melting point 255° C.

Potency: 80.2%; 1,2-Dichloroethane: 7.5% (gas chromatography).

EXAMPLE 3

6-Hydroxy-2-(4-hydroxyphenyl)-3-[4-(2-piperidinoethoxy)benzoyl]-benzo[b]thiophene Hydrochloride Methylene Chloride Solvate (Crystal Form IV)

A mixture of the compound prepared as described in Preparation 1 (7.54 grams) in methylene chloride (10 mL) and the acid chloride prepared as described in Preparation 4 (140 mL, 0.21 M solution in methylene chloride) was placed in a sealed reaction vessel (Hastalloy Parr). The solution was cooled to 0° C. and treated with boron trichloride (7.2 mL). The resulting reaction mixture was stirred at room temperature. After three hours, the reaction was cooled in an ice bath for 10 minutes. A second portion of boron trichloride (4.8 mL) was added to the reaction mixture, and the mixture was heated to 75° C. After 2.5 hours, the reaction mixture was cooled to about 15° C. The cool mixture was treated with tetrahydrofuran (15 mL) and methanol (45 mL). This mixture was stirred for about one hour at 18° C., producing a crystalline solid. The crystalline solid was removed by filtration, rinsed with cold methanol (45 ML), and dried in vacuo at 40° C. for 18 hours, to give 12.5 grams of the title compound. The X-ray powder diffraction pattern is identical to that reported in Table 4. Melting point 207° C.

Potency: 81.8%;

Methylene chloride: 0.4 molar equivalents ($^1$H NMR).

EXAMPLE 4

6-Hydroxy-2-(4-hydroxyphenyl)-3-[4-(2-piperidinoethoxy)benzoyl]-benzo[b]thiophene Hydrochloride 1,2-Dichloroethane Solvate (Crystal Form I)

A mixture of the compound prepared as described in Preparation 3 (15 g) and dimethylformamide (0.2 mL) in 1,2-dichloroethane (250 mL) was cooled to 0° C. Phosgene (8.25 mL) was condensed in a cold, jacketed addition funnel (−10° C.), and added to the cold mixture over a period of two minutes. The resulting mixture was heated to about 47° C. After about two and one half hours, the reaction was assayed by HPLC for completion. Additional phosgene may be added to drive the reaction to completion. Excess phosgene was removed by vacuum distillation at 30–32° C. and 105–110 mm Hg.

After about three to four hours, the reaction solution was treated with the compound prepared as described in Preparation 1 (13.52 g). The resulting solution was cooled to 0° C. Boron trichloride (12.8 mL) was condensed in a graduated cylinder, and added to the cold reaction mixture. After eight hours at 0° C., the reaction solution was treated with additional boron trichloride (12.8 mL). The resulting solution was heated to 30° C. After 15 hours, the reaction was monitored for completion by HPLC.

A mixture of ethanol and methanol (125 mL, 95:5, 3A) was heated to reflux, and treated with the reaction solution from above over a 60 minute period. Upon complete addition, the acylation/demethylation reaction flask was rinsed with additional 3A ethanol (30 mL). The resulting slurry was allowed to cool to room temperature with stirring. After one hour at room temperature, the crystalline product was filtered, washed with 3A ethanol (75 mL), and dried at 40° C. in vacuo to give 25.9 g of the title compound. The X-ray powder diffraction pattern is reported in Table 1. Melting point 261° C.

Potency: 87.1%; 1,2-Dichloroethane: 0.55 molar equivalents ($^1$H NMR).

EXAMPLE 5

6-Hydroxy-2-(4-hydroxyphenyl)-3-[4-(2-piperidinoethoxy)benzoyl]-benzo[b]thiophene Hydrochloride Chlorobenzene Solvate (Crystal Form III)

A solution of the compound prepared as described in Preparation 1 (2.92 grams) and the acid chloride prepared as described in Preparation 4 (3.45 grams) in chlorobenzene (52 mL) was cooled to about 0° C. The cold solution was treated with boron trichloride (2.8 mL). The resulting mixture was mechanically stirred at about 0° C. After three hours, additional boron trichloride (2.8 mL) was added, and the reaction mixture was allowed to warm to room temperature. After about 16–20 hours, the reaction mixture was cooled to 0° C. The cold reaction was quenched by the slow addition of ethanol (26 mL) over 30 minutes. During the addition of the alcohol, a crystalline solid formed. Upon complete addition of the alcohol, the resulting mixture was stirred at room temperature for one hour. The crystalline solid was removed by filtration, washed with cold ethanol (25 mL), and dried in vacuo at 40° C. to give 5.94 grams of the title compound as a yellow solid. The X-ray powder diffraction pattern is identical to that reported in Table 3. Melting point 247° C.

Potency: 78.6%; Chlorobenzene: 12.3% (HPLC).

EXAMPLE 6

6-Hydroxy-2-(4-hydroxyphenyl)-3-(4-(2-piperidinoethoxy)benzoyl]-benzo[b]thiophene Hydrochloride 1,2-Dichloroethane Solvate (Crystal Form II)

A mixture of the compound prepared as described in Preparation 1 (2.92 g), the compound prepared as described in. Preparation 4 (3.45 g), and 1,2-dichloroethane (52 mL) was cooled to about 0° C. Boron trichloride gas was condensed into a cold graduated cylinder (2.8 mL), and added to the cold mixture described above. After eight hours at 0° C., the reaction mixture was treated with additional boron trichloride (2.8 mL). The resulting solution was heated to 35° C. After 16 hours, the reaction was complete.

Methanol (30 mL) was treated with the reaction mixture from above over a 20-minute period, causing the methanol to reflux. The resulting slurry was stirred at 25° C. After one hour, the crystalline product was filtered, washed with cold methanol (8 mL), and dried at 40° C. in vacuo to give 5.14 g of the title compound. The X-ray powder diffraction pattern is reported in Table 2. Melting point 225° C.

Potency: 86.8%; 1,2-Dichloroethane: 6.5% (gas chromatography).

EXAMPLE 7

6-Hydroxy-2-(4-hydroxyphenyl)-3-[4-(2-piperidinoethoxy)benzoyl]-benzo[b]thiophene Hydrochloride The compound prepared as described in EXAMPLE 4 (4.0 grams) was slurried in methanol (30 mL) at room temperature. The resulting mixture was treated with a solution of sodium hydroxide (0.313 grams) in methanol (10 mL). After complete dissolution, activated carbon (0.4 grams, Darco G-60, Aldrich Chem. Co., Inc., Milwaukee, Wis.) was added to the solution. After 30 minutes, the slurry was filtered through Whatman #1 filter paper precoated with diatomaceons earth (Hyflo Super Cel®, Aldrich Chem. Co.). The filter cake was rinsed with methanol (10 mL). The combined filtrate was treated (dropwise) with 2N hydrochloric acid (4 mL). The resulting slurry was stirred for 60 minutes at room temperature, and filtered. The filter cake was rinsed with cold methanol (14 mL, 0° C.), and dried in vacuo at 60° C. for about 18 hours to give 3.00 grams of an off-white free flowing powder. Melting point 262° C.

Potency: 99.1%; Related substances: 0.85%

EXAMPLE 8

6-Hydroxy-2-(4-hydroxyphenyl)-3-[4-(2-piperidinoethoxy)-benzoyl]benzo[b]thiophene Hydrochloride 1,2-Dichloroethane Solvate (Crystal Form I)

A saturated solution of 6-hydroxy-2-(4-hydroxyphenyl)-3-[4-(2-piperidinoethoxy)benzoyl]benzo[b]thiophene hydrochloride was produced by stirring a slurry of the compound prepared as described in Example 7 in methanol at room temperature overnight. This mixture was filtered (Whatman #1 filter paper). A portion of the filtrate (20–25 mL) was placed in a 50 mL Erlenmeyer flask. This flask was placed within a glass jar (3.5 in.×4 in.) containing 1,2-dichloroethane (about 10 mL). The jar was sealed and the combination was allowed to stand at room temperature. After 24 hours, single crystals had crystallized from the methanol solution. These crystals were filtered and dried in vacuo. Melting point 273° C. The crystal structure was determined with a Siemens R3m/V automated four-circle diffractometer using monochromatic copper radiation ($\lambda$=1.54178Å). The crystal structure was solved using the direct methods routine TREF of the SHELXTL PLUS program library. Full-matrix least-squares refinement was conducted with anisotropic temperature factors for all atoms except hydrogens, which were included at calculated positions with isotropic temperature factors. The final R-factor was 8.02%. The crystal data is shown below.
Crystal Data

| Space group | C2/C |
|---|---|
| Unit all dimensions | a = 20.720(7) Å |
| | b = 9.492(2) Å |
| | c = 28.711(4) Å |
| | $\beta$ = 96.50(2)° |
| Volume | 5610(2) Å$^3$ |
| Density (calc.) | 1.409 mg/m$^3$ |
| Absorption coefficient | 3.951 mm$^{-1}$ |

The X-ray structure clearly shows that the crystalline material is a 1,2-dichloroethane solvate having a 1:2 ratio of molecules of 1,2-dichloroethane to molecules of 6-hydroxy-2-(4-hydroxyphenyl)-3-[4-(2-piperidinoethoxy)benzoyl]-benzo[b]-thiophene hydrochloride.

EXAMPLE 9

6-Hydroxy-2-(4-hydroxyphenyl)-3-[4-(2-piperidinoethoxy)-benzoyl]benzo[b]thiophene Hydrochloride 1,2,3-Trichloropropane Solvate (Crystal Form II)

A mixture of the compound prepared as described in Preparation 1 (2.70 g), the compound prepared as described in Preparation 4 (3.60 g), and 1,2,3-trichloropropane (50 mL) was treated with boron trichloride (2.6 mL). After three hours at 20–25° C., the reaction mixture was treated with additional boron trichloride (2.6 mL). After about 18 hours, the reaction mixture was treated with tetrahydrofuran (15 mL) followed by the slow addition of methanol (15 mL). After these additions were complete, the resulting mixture was stirred at room temperature. After one hour, the crystalline solid was collected by filtration, washed with cold methanol (10 mL), and dried at 50° C. in vacuo to give 4.13 g of the title compound. The X-ray powder diffraction pattern was identical to that reported in Table 2. Melting point 236° C.

Potency: 78.9%; 1,2,3-Trichloropropane: 0.5 molar equivalents ($^1$H NMR).

EXAMPLE 10

6-Hydroxy-2-(4-hydroxyphenyl)-3-[4-(2-piperidinoethoxy)-benzoyl]benzo[b]thiophene Hydrochloride Chloroform Solvate (Crystal Form IV)

The title compound (4.42 g) was prepared using the procedure described in EXAMPLE 9, except the reaction solvent was chloroform (50 mL). The X-ray powder diffraction pattern was identical to that reported in Table 4. Melting point 258° C.

Potency: 80.4%; Chloroform: 0.42 molar equivalents ($^1$H NMR).

EXAMPLE 11

6-Hydroxy-2-(4-hydroxyphenyl)-3-[4-(2-piperidinoethoxy)-benzoyl]benzo[b]thiophene Hydrochloride A solution of sodium hydroxide (0.313 g) in methanol (10 mL) was diluted with additional methanol (50 mL). This solution was treated with the compound prepared as described in EXAMPLE 6 (4.0 g). After 45 minutes at room temperature, the solution was filtered (Whatman #1 filter paper) and the filter paper rinsed with methanol (3 mL). The filtrate was treated with 2 N hydrochloric acid (4 mL), producing a crystalline slurry. After 1 ½ hours, this crystalline product was filtered, washed with methanol (5 mL), and dried at 45–50° C. in vacuo to give 2.103 g of the title compound. The X-ray powder diffraction pattern was identical to that reported in Table 5. Melting point 261° C.

Potency: 96.5%.

EXAMPLE 12

6-Hydroxy-2-(4-hydroxyphenyl)-3-[4-(2-piperidinoethoxy)-benzoyl]benzo[b]thiophene Hydrochloride A solution of sodium hydroxide (0.313 g) in methanol (10 mL) was diluted with additional methanol (40 mL) and water (10 mL). This solution was treated with the compound prepared as described in EXAMPLE 5 (4.0 g). The resulting solution was extracted with hexane (2×50 mL) to remove the chlorobenzene. The methanolic phase was treated with 2 N hydrochloric acid (4 mL), producing a crystalline slurry. After one hour, the crystalline product was filtered, washed with methanol (5 mL), and dried at 60° in vacuo to give 2.23 g of the title compound. The X-ray powder diffraction pattern was identical to that reported in Table 5. Melting point 272° C.

Potency: 97.5%; Residual Chlorobenzene: <0.3% (HPLC); Related substances: 0.94%.

We claim:
1. A process for preparing a crystalline solvate of a compound of the formula:

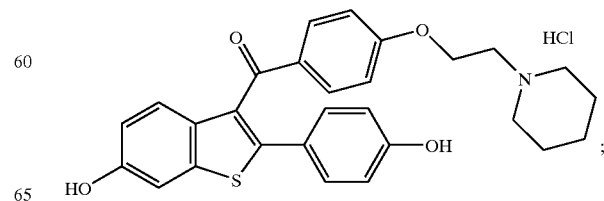

which comprises:

a) acylating a benzothiophene of the formula:

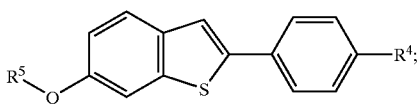

wherein:
R⁴ is $C_1$–$C_4$ alkoxy; and
R⁵ is $C_1$–$C_4$ alkyl;
with an acylating agent of the formula:

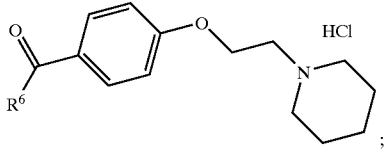

wherein:
R⁶ is chloro, bromo, or hydroxyl;
in the presence of a solvent and boron trichloride;

b) dealkylating the acylated benzothiophene by reacting said acylated benzothiophene with additional boron trichloride to prepare a compound of the formula:

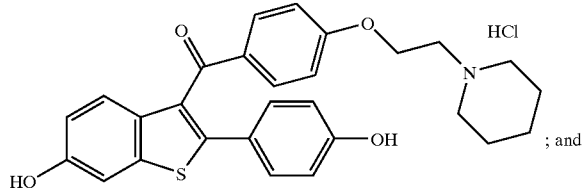

c) isolating the crystalline solvate.

2. The process of claim 1 wherein R⁶ is chloro.

3. The process of claim 2 wherein R⁴ is methoxy and R⁵ is methyl.

4. The process of claim 3 wherein the acylation is conducted in the presence of 2–5 molar equivalents of $BCl_3$.

5. The process of claim 3 wherein the dealkylation is conducted in the presence of 3–10 molar equivalents of $BCl_3$.

6. The process of claim 3 where in the solvent is 1,2-dichlorethane.

7. A process for preparing a crystalline solvate of the formula:

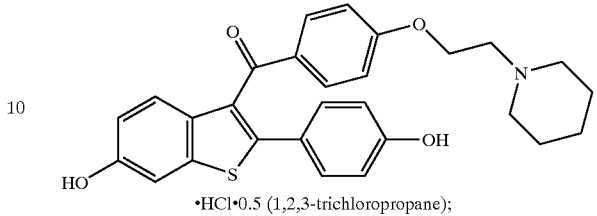

·HCl·0.5 (1,2,3-trichloropropane);

which comprises the process of claim 1 wherein the solvent is 1,2,3-trichloropropane and which further comprises the step of adding methanol to the product mixture of step b) prior to isolating the crystalline solvate.

8. The process of claim 7 wherein R⁴ is methoxy, and R⁵ is methyl.

9. A process for preparing a crystalline solvate of the formula:

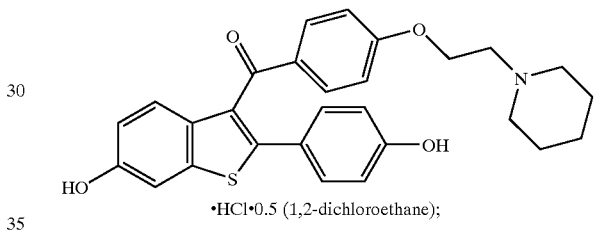

·HCl·0.5 (1,2-dichloroethane);

which comprises the process of claim 1 wherein the solvent is 1,2-dichloroethane and which further comprises the step of adding methanol to the product mixture of step b) prior to isolating the crystalline solvate.

10. The process of claim 9 wherein R⁴ is methoxy, and R⁵ is methyl.

* * * * *